United States Patent [19]

Kulp

[11] 4,264,616
[45] Apr. 28, 1981

[54] 2-IODOACETYLIMINO-3-METHYL-5-TRI-FLUOROMETHYL-1,3,4-THIADIAZOL-4-INE AND USE AS A FUNGICIDE

[75] Inventor: Richard A. Kulp, Littleton, Colo.

[73] Assignee: Gulf Oil Corporation, Pittsburgh, Pa.

[21] Appl. No.: 182,376

[22] Filed: Aug. 29, 1980

[51] Int. Cl.³ .................... A01N 43/82; C07D 285/12
[52] U.S. Cl. .................................. 424/270; 548/138; 548/139
[58] Field of Search ................. 424/270; 548/138, 139

[56] References Cited

U.S. PATENT DOCUMENTS

| 2,783,241 | 2/1957 | Young et al. | 548/139 |
| 3,522,267 | 7/1970 | Duerr et al. | 548/139 |
| 3,564,002 | 2/1971 | Remers et al. | 548/139 |
| 3,728,354 | 4/1973 | Rucker et al. | 548/139 |
| 4,092,148 | 5/1978 | Cebalo | 548/139 |

Primary Examiner—Alton D. Rollins
Attorney, Agent, or Firm—Carl A. Cline

[57] ABSTRACT

The novel compound having the structural formula,

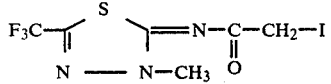

which may be conveniently synthesized from readily available chemical substances is disclosed to be useful as a fungicide, particularly in combating fungus diseases of plants by application to soil or plant foliage.

3 Claims, No Drawings

2-IODOACETYLIMINO-3-METHYL-5-TRIFLUOROMETHYL-1,3,4-THIADIAZOL-4-INE AND USE AS A FUNGICIDE

DESCRIPTION OF THE INVENTION

Nearly all soils are infested with fungi which cause damping-off of crop seedlings and many species of fungi which cause wilts and root rots are very common and widely distributed in soils. Other fungus diseases of plants are spread by air-borne spores. Fungus diseases are combated by various means, none of which has resulted in the eradication of any fungus disease. The pathogenic fungi have the ability to adapt to changes in soil conditions, the use of disease-resistant strains of crops and the use of fungicides, so that only temporary control of fungus diseases is achieved. Although heavy metal containing compounds have provided the best control of fungi in many instances, the toxic residues left by these compounds make them undesirable for continued use. The effectiveness of organic compounds which leave no toxic residues is in all instances temporary because of the adaptability of the fungi to the presence of these substances. It has been found advisable to make frequent changes from one fungicide to another, so as to avoid the development of resistance by the fungi.

I have discovered a novel compound which is relatively unrelated chemically to other agricultural fungicides, so that it is particularly useful in a program of rotation of fungicidal agents for the purpose of chemical control of fungus diseases of plants. In addition to providing a novel fungicidal agent, the present invention includes the method of combating fungus diseases of plants which comprises applying to the locus of the plants an effective amount of 2-iodoacetylimino-3-methyl-5-trifluoromethyl-1,3,4-thiadiazol-4-ine. Preparation and use of the novel fungicide are described and illustrated specifically in the following discussion.

SYNTHESIS OF THE FUNGICIDE

The novel fungicide of this invention may be conveniently prepared from commonly available substances by means of the reaction scheme outlined below:

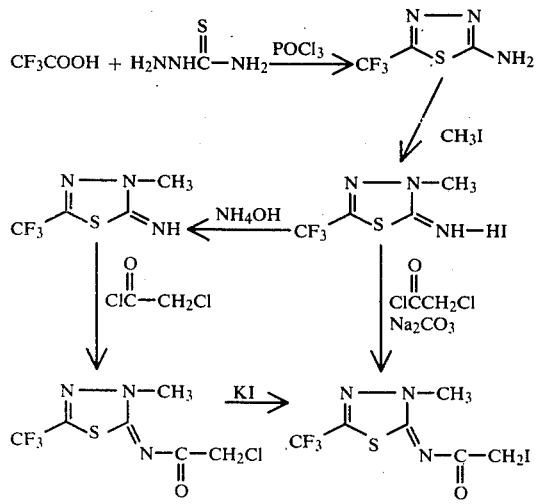

The scheme is illustrated by means of the following specific procedures:

1. Preparation of 2-Amino-5-trifluoromethyl-1,3,4-thiadiazole

A three-liter reaction flask fitted with a mechanical stirrer, heating mantle, dropping funnel, thermometer and water-cooled condenser connected to a caustic trap was charged with 228 g (2.5 mole) of thiosemicarbazide, 1260 ml of 1,4-dioxane and 285.1 g (2.5 mole, 193 ml) of trifluoroacetic acid. The dropping funnel contained 383.8 g (2.5 mole, 229 ml) of phosphorus oxychloride which was added to the reaction flask over a period of 30 minutes. The resulting thick slurry was heated slowly to reflux with rapid evolution of hydrogen chloride gas. The slurry thinned with separation of the product as a heavy syrup. Total reflux time required about four hours until the gas evolution ceased. The dioxane was decanted and then 1700 ml of water was added to the residue. The mixture was cooled to 20° C. and made basic with 50% sodium hydroxide (~225 ml) to pH 9. The slurry was cooled to 10° C. and collected on a filter funnel. The cake was washed with cold water and dried in the oven. There was obtained 305 g, Mp 219°–220.5°, yield 72.1%. The proton NMR recorded in $Me_2SO\text{-}d_6$ consisted of a peak at 7.9∂ ($NH_2$) with respect to tetramethylsilane.

2. Preparation of 2-Imino-3-methyl-5-trifluoromethyl-1,3,4-thiadiazole-4-ine A three-liter reaction flask fitted with a mechanical stirrer, thermometer and a calcium sulfate drying tube was charged with 411.2 g (2.43 mole) of 2-Amino-5-trifluoromethyl-1,3,4-thiadiazole, 400 ml of dimethylformamide and 517.5 g (3.65 mole, 227 mls) of iodomethane. The solution was heated at 50° C. for 16 hours and then concentrated under vacuum to remove some of the dimethylformamide which yielded a thick slurry. Tolune (~6 liter) was added and the slurry was stirred for 30 minutes. The slurry was filtered and the cake was washed with toluene. The total weight was 824 g. This salt was dissolved in 3500 ml of water and the solution was extracted with ether to remove impurities. The solution was made basic (pH 9) with ammonium hydroxide and the organic layer was extracted with two portions of chloroform. The chloroform extracts were dried over anhydrous sodium sulfate and the chloroform was removed on a rotary evaporator. There was obtained 356.5 g oil, yield 80.1% which will crystallize, Mp 42°–43°. A second crop is available to bring the yield to 81.9%.

3. Preparation of 2-Chloroacetylimino-3-methyl-5-trifluoromethyl-1,3,4-thiadiazol-4-ine A five-liter reaction flask fitted with a mechanical stirrer, thermometer, dropping funnel and a nitrogen purge was charged with 2000 ml of tetrahydrofuran, 356.5 g (1.95 mole) of 2-imino-3-methyl-5-trifluoromethyl-1,3,4-thiadiazol-4-ine and 206.4 g (2.04 mole, 284 ml) of triethylamine. A 231 g portion (2.04 mole, 163 ml) of chloroacetyl chloride was added from the dropping funnel over a period of three hours while the temperature was maintained between 10°–15° C. The resulting mixture was stirred at 25° C. for 16 hours. The solid was removed by filtration and washed with tetrahydrofuran. The tetrahydrofuran was removed on the rotovap and the oil was dissolved in 1250 ml of ethyl acetate. The resulting organic solution was washed with 300 ml of 10% sodium carbonate, 250 ml of water 250 ml of 1% hydrochloric acid, 250 ml of water and finally with 300 ml of saturated sodium chloride solution. The organic layer was dried over anhydrous sodium sulfate and the ethyl acetate was removed on a rotary evaporator. The residue was crystallized from hexane to give 426.5 g of product, yield 84.2%, Mp 46°–48° C.

4. Preparation of 2-Iodoacetylimino-3-methyl-5-trifluoromethyl-1,3,4-thiadiazol-4-ine A five-liter reaction flask fitted with a mechanical stirrer, thermometer and a reflux condenser was charged with 643.5 g (2.48 mole) of 2-chloroacetylimino-3-methyl-5-trifluoromethyl-1,3,4-thiadiazol-4-ine, 2500 ml of acetone and 432.5 g (2.61 mole) of potassium iodide. The resulting mixture was heated at reflux for four hours and then cooled to 30° C. The mixture was filtered to remove the inorganic salts and the cake was washed with acetone. The acetone was removed on a rotary evaporator and the residue was crystallized from hexane (~1500 ml). The product was collected on a filter and the cake was washed with hexane. There was obtained 805.5 g of product, yield 92.8% Mp 68°–70°.

A shortened synthesis procedure employs the two steps illustrated below:

1. Preparation of 2-Imino-3-methyl-5-trifluoromethyl-1,3,4-thiadiazol-4-ine hydroiodide salt A three-liter reaction flask fitted with a mechanical stirrer, thermometer and a calcium sulfate drying tube was charged with 290 g (1.71 mole) of 2-amino-5-trifluoromethyl-1,3,4-thiadiazole, 600 ml of dimethylformamide and 255.5 g (1.8 mole, 112 ml) of iodomethane. The solution was stirred at 25° C. for 16 hours and then concentrated under vacuum to obtain a thick slurry. This was treated with 400 ml of ethyl acetate and the slurry was cooled to 10° C. The mixture was filtered and the cake was washed with ethyl acetate. The mother liquor was concentrated to obtain a second crop. The total weight of isolated product was 284 g, yield 53.4%.

2. Preparation of 2-Iodoacetylimino-3-methyl-5-trifluoromethyl-1,3,4-thiadiazol-4-ine A three-liter reaction flask fitted with a mechanical stirrer, thermometer, dropping funnel and a calcium sulfate drying tube was charged with 750 ml of ethyl acetate, 276 g (0.89 mole) of 2-imino-3-methyl-5-trifluoromethyl-1,3,4-thiadiazol-4-ine hydroiodide salt and 138 g (1.3 mole) of sodium carbonate. The dropping funnel contained 105.3 g (0.93 mole, 74.3 ml) of chloroacetyl chloride which was added over a period of 30 minutes while the temperature rose to 55° C. The reaction mixture was stirred at 25° C. for 16 hours. The resulting solution was washed with 500 ml of water, 250 ml of dilute hydrochloric acid and finally with 400 ml of water. After the ethyl acetate solution was dried over anhydrous sodium sulfate, the solvent was removed on a rotary evaporator. The residue was recrystallized from 1500 ml of hexane. The solution was cooled to 10° C., the slurry was collected on a filter and the cake was washed with hexane. The hexane filtrate was concentrated to obtain a second crop. After drying, there was obtained 151 g of crude product, Mp 68°–70°, yield 48.3%. A sample recrystallized from hexane gave product with Mp 70°–72° C. Analysis calculated for $C_6H_5F_3IN_3OS$: C, 20.53; H, 1.44; F, 16.24; N, 11.97; S, 9.16. Found: C, 20.68; H, 1.48; F, 17.63; N, 11.84; S, 9.43. MS m/e 351(M+, 12), 332(1), 224(3), 210(100), 196(12), 169(5), 141(8), 128(5), 127(11), 86(4), 69(8), 53(13), 43(10).

USE OF THE FUNGICIDE

The use of the novel fungicide to combat plant diseases is illustrated by means of the following description of use under controlled experimental conditions.

The procedure used to demonstrate use as a soil fungicide may be illustrated as follows:

A. Preparation of Inoculum 100 g of vermiculite is placed in a 2 liter flask and moistened with 162 ml potato-dextrose broth (Difco brand). The flask are stopped with a cotton plug and sterilized at 15 lb pressure for 20 min. After the flasks are cool they are inoculated with *Rhizoctonia sclerotia* and mycelium, and incubated at room temperature. Every 3 days the cultures are shaken to insure even growth of the organism. These cultures can be used to inoculate test soil after 12 days and remain useable for 6–8 weeks.

B. Preparation of Test Soil

Sandy oil is pasteurized at 200° F. After cooling 60 lbs are placed in a cement mixer and mixed with the contents of one vermiculite culture of Rhizoctonia.

C. Evaluation of Effect of Fungicide on Seeds

The inoculated soil is then dispensed into aluminum trays—one 8 oz. oaken bucket full/tray and then sprayed with the herbicide screen. After spraying, the soil is shaken in a 32 oz. plastic carton to mix the chemical. Ten cotton seeds are planted in the soil ¼" from the bottom of a 16 oz. oaken carton. The soil is watered with approx. 50 ml H₂O (the actual amount depends upon soil moisture content) placed in the greenhouse. Results are determined after 2–3 weeks using the following rating scale:

| Emergence vs. Disease Control A/B | |
|---|---|
| A | B |
| 0 = no emergence | 0 = all plants diseased |
| 1 = 1–3 plants emerged | 1 = 1–30% healthy plants |
| 2 = 4–6 plants emerged | 2 = 31–36% healthy plants |
| 3 = 7–9 plants emerged | 3 = 61–90% healthy plants |
| 4 = 10 plants emerged | 4 = all plants healthy |

The fungicide was applied to cotton seeds at various rates, from 6.25 ppm to 100 ppm by weight in two separate tests, according to the above procedure. The results obtained are tabulated below.

| First Test | | Second Test | |
|---|---|---|---|
| Rate (ppm) | A/B | Rate (ppm) | A/B |
| 100 | 3/1 (Roots pruned) | 50 | 4/4 (Phytotoxic) |
| 50 | 3/3 | 25 | 3/4 |
| 25 | 4/3 | 12.5 | 3/0 |
| 12.5 | 4/1 | 6.25 | 2/0 |
| 6.25 | 0/0 | | |

The compound was also evaluated according to the above procedure against *R. solani* using twelve crop species. Emergence and disease control were recorded. Values given are A/B for two replications.

| Crop | Results at Three Application Rates | | | | | |
|---|---|---|---|---|---|---|
| | 25 ppm | | 12.5 ppm | | 6.25 ppm | |
| Alfalfa | 4/2* | 4/3* | 4/0 | 4/1 | 4/0 | 4/0 |
| Soybean | 4/3* | 4/2* | 4/1 | 4/0 | 4/0 | 4/0 |
| Sugar beet | 4/4 | 4/4 | 4/0 | 4/0 | 4/0 | 4/0 |
| Cabbage | 4/4 | 4/4 | 4/2 | 4/1 | 4/1 | 4/1 |
| Carrot | 4/4 | 4/4 | 4/1 | 4/1 | 4/1 | 4/1 |
| Cotton | 4/4 | 4/4 | 4/0 | 4/0 | 4/0 | 4/0 |
| Cucumber | 4/2* | 4/3* | 4/0 | 4/0 | 4/0 | 4/0 |
| Pea | 4/4* | 4/4* | 4/2* | 4/2* | 4/1 | 4/1 |
| Lettuce | 4/2* | 4/2* | 4/0 | 4/0 | 4/1 | 4/1 |
| Oat | 4/3* | 4/3* | 4/0 | 4/0 | 4/0 | 4/0 |
| Okra | 4/4* | 4/4* | 4/0 | 4/0 | 4/0 | 4/2 |
| Spinach | 4/3 | 4/3 | 4/0 | 4/0 | 4/0 | 4/1 |

*Phytotoxicity observed

The fungicide was also tested by a procedure of the type illustrated above, except that soil which was naturally infested with Pythium was used and "Perfection" variety of peas were planted to test protection from preemergence damping-off. The following results were obtained:

| Rate (ppm) | % emerged |
|---|---|
| 50 | 100 |
| 25 | 97 |
| 12.5 | 86 |
| Untreated 0 | 46 |

A series of seed treatment tests were performed using barley seed artificially infected with *Helminthosporium sativum* and barley seed naturally infected with loose smut and other fungi, causing seed decay and seedling blight. At 1% fungicide by weight of seen no emergence occurred. Lower rates were therefore employed. Results were as follows:

USE AS SEED PROTECTANT
ON ARTIFICIALLY INFECTED BARLEY
PLANTED IN SANDY SOIL (100 seeds in each test)

| | Rate (% ai by wt) | % emerged | % diseased | % control |
|---|---|---|---|---|
| | 0.25 | 87 | 12 | 82 |
| | 0.10 | 91 | 12 | 83 |
| | 0.10 | 86 | 16 | 81 |
| | 0.05 | 90 | 34 | 62 |
| Use as 100% active | 0.52 | | | 94 (Phytotoxic) |
| | 0.26 | | | 87 |
| | 0.13 | | | 87 |
| | 0.06b | | | 52 |
| | 0.0325 | | | 20 |
| Use as 20% active w/attaclay | 0.52 | | | 100 (Phytotoxic) |
| | 0.26 | | | 78 (Phytotoxic) |
| | 0.13 | | | 59 |
| | 0.065 | | | 23 |
| | 0.0325 | | | 18 |

The following treatments were tested similarly except that the barley was planted in non-sterile greenhouse potting soil.

| | Rate (% ai by wt) | No. emerged (of 50 planted) | No. healthy (of 50 planted) |
|---|---|---|---|
| Use as 100% active | 0.52 | 27 | 27 |
| | 0.26 | 32 | 32 |
| | 0.13 | 37 | 37 |
| | 0.065 | 44 | 43 |
| Use as 20% active w/attaclay | 0.0325 | 42 | 37 |
| | 0.52 | 9 | 9 |
| | 0.26 | 29 | 29 |
| | 0.13 | 41 | 41 |
| | 0.065 | 36 | 34 |
| | 0.0325 | 35 | 32 |

In another test the fungicide was applied as a 50% dust formulation on barley seed artificially infected with *H. sativum*. One hundred seeds per treatment were planted in both sandy soil and greenhouse potting soil. Results appear below:

RESULTS OF USE AS DUST TO TREAT BARLEY INFECTED WITH *HELMINTHOSPORIUM SATIVUM*

| Compound | Rate (oz ai/bu) | Sandy Soil | | | Greenhouse Potting Soil | | |
|---|---|---|---|---|---|---|---|
| | | No. emerged | No. diseased | % control | No. emerged | No. healthy | % of ck. untreated |
| Use as (50% active w/Aero Dust F) | 1 | 79 | 8 | 90 | 79 | 77 | 214 |
| | ¾ | 77 | 9 | 82 | 73 | 69 | 192 |
| | ½ | 73 | 19 | 74 | 71 | 70 | 194 |

This same dust formulation of the fungicide was tested on barley seed naturally infected with loose smut and other fungi causing seed decay and seedling blight. Five hundred seeds per treatment were planted in non-sterile greenhouse potting soil. Results appear below:

| Compound | Rate (oz ai/bu) | No. healthy | (as % of check) | Smutted heads (No.) | (% of total) |
|---|---|---|---|---|---|
| (Use as 50% Dust) | ¾ | 474 | 105 | 85 | 18 |
| Untreated | | 450 | | 92 | 21 |

The effectiveness of the fungicide in vitro was evaluated at concentrations of 3 ppm to 25 ppm in nutrient media inoculated and incubated with various organisms. The general procedure is specifically illustrated below:

Preparation of Media
Materials for making the media are as follows:

24 g. potato dextrose broth
2 g neopeptone

-continued

| Preparation of Media |
| --- |
| Materials for making the media are as follows: |
| 2 g malt broth (dehydrated) |
| 1000 ml deionized water |

All materials are dissolved in the water. The media is dispensed into 1 oz. bottles—20 ml/bottle, capped and sterilized in the autoclave for 20 min.

Evaluation of the Fungicide

A. 0.1 ml of formulated chemical (formulated in greenhouse surfactant) is dispensed into a bottle of media using the disposable pipetting unit.

B. The test chemical solution is inoculated, eg, with 5 drops of a suspension of *Penicillium digitatum* which is prepared as follows:

5-10 ml of sterile deionized $H_2O$ and one drop of Tween 20 are added aseptically to a slant of *P. digitatum* with a sterile loop. The spore suspension produced by stirring is added aseptically to 150 ml. approx. of sterile deionized $H_2O$ which is then used to inoculate the test chemical solution.

C. After inoculation the samples are incubated at room temperature for 2 weeks. Results are determined using the following rating system:
 0=fungus growth maximum
 1=fungus growth fair
 2=fungus growth slight
 3=trace of fungus growth
 4=no growth of fungus
Results are given below for tests with three organisms:

|  | Aspergillus sp. | Penicillium sp. | | | *Botrytis cinerea* | | |
| --- | --- | --- | --- | --- | --- | --- | --- |
| Conc'n. | 25 ppm | 25 ppm | 10 ppm | 3 ppm | 25 ppm | 10 ppm | 3 ppm |
| Rating | 4 | 4 | 4 | 0 | 4 | 4 | 0 |

The fungicide is usually applied in combination with inert carriers or diluents, as in aqueous sprays, granules and dust formulations in accordance with established practice in the art. An aqueous spray is usually prepared by mixing a wettable powder or emulsifiable concentrate formulation of the fungicide with a relatively large mount of water to form a dispersion.

Wettable powders comprise intimate, finely divided mixtures of fungicide, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the fungicide compounds comprise in each instance, a solution of fungicide compound in a liquid carrier which is a mixture of waterimmiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The fungicide formulations desirably contain from 0.1 percent to 95 percent by weight of the fungicide compound and from 0.1 to 75 percent of an inert carrier or surfactant. The direct application to plant seeds prior to planting may be accomplished in some instances by mixing either powdered solid fungicide or a dust formulation with seed to obtain a substantially uniform coating which is very thin and comprises only one or two percent by weight or less, based on the weight of the seed. In some instances, however, a nonphytotoxic solvent, such as methanol is conveniently employed as a carrier to facilitate the uniform distribution of fungicide on the surface of the seed.

When a compound is to be applied to the soil, as for pre-emergence protection, granular formulations or dusts are sometimes more convenient than sprays. A typical granular formulation comprises the fungicide compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

I claim:

1. The fungicidal compound 2-Iodoacetylimino-3-methyl-5-trifluoromethyl-1,3,4-thiadiazol-4-ine.

2. The fungicidal formulation which comprises from 0.1 percent to 95 percent by weight of the compound of claim 1 and from 0.1 to 75 percent by weight of an inert carrier or surfactant.

3. The method of combating fungus diseases of plants which comprises applying to the locus of the plants an effective amount of the compound of claim 1.

* * * * *